| United States Patent [19] | [11] Patent Number: 4,902,497 |
| Crisanti et al. | [45] Date of Patent: Feb. 20, 1990 |

[54] ORAL COMPOSITIONS

[75] Inventors: Mark M. Crisanti, Cincinnati; Anthony C. Lanzalaco, Fairfield; Richard J. Sunberg, Oxford, all of Ohio

[73] Assignee: The Procter & Gamble Company, Cincinnati, Ohio

[21] Appl. No.: 162,524

[22] Filed: Mar. 1, 1988

[51] Int. Cl.$^4$ .......................... A61K 7/16; A61K 7/18
[52] U.S. Cl. .......................... 424/52; 424/49; 424/55
[58] Field of Search ..................... 424/49–58

[56] References Cited

U.S. PATENT DOCUMENTS

| 3,105,798 | 10/1963 | Holliday et al. | 167/93 |
| 3,549,677 | 12/1970 | Griesbstein et al. | 260/429.7 |
| 3,560,608 | 2/1971 | Griebstein et al. | 424/49 |
| 3,939,262 | 2/1976 | Kim | 424/49 |
| 4,007,260 | 2/1977 | Kim | 424/52 |
| 4,289,753 | 9/1981 | Dyroff et al. | 424/48 |
| 4,308,252 | 12/1981 | Tomaich et al. | 424/52 |
| 4,335,102 | 6/1982 | Nakashima et al. | 424/52 |
| 4,338,346 | 7/1982 | Brand | 424/52 |
| 4,363,794 | 12/1982 | Ochiai et al. | 424/52 |
| 4,568,540 | 2/1986 | Asano et al. | 424/52 |
| 4,592,487 | 6/1986 | Simon et al. | 222/94 |
| 4,693,888 | 9/1987 | Miyahara et al. | 424/52 |
| 4,702,904 | 10/1987 | Maeyama et al. | 424/52 |

Primary Examiner—Shep K. Rose
Attorney, Agent, or Firm—Richard C. Witte; Jack D. Schaeffer; Douglas C. Mohl

[57] ABSTRACT

Methods for reducing calculus are disclosed utilizing oral compositions containing stannous ions complexed with certain carboxylic acids or polyhydric alcohols.

5 Claims, No Drawings

ORAL COMPOSITIONS

TECHNICAL FIELD

The present invention relates to methods of reducing calculus using oral compositions such as liquid dentifrices, toothpastes and mouthwashes containing stannous ions complexed with certain carboxylic acids or polyhydric alcohols.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consist of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Patent 490,384, Feb. 15, 1937, discloses oral compositions containing ethylenediaminetetraacetic acid, nitrilotriacetic acid and related compounds as anticalculus agents. U.S. Pat. No. 3,678,154, July 18, 1972 to Widder et al. discloses oral compositions containing certain polyphosphonates and fluoride. U.S. Pat. No. 3,737,533, June 5, 1973 to Francis discloses oral compositions containing certain carbonyl diphosphonates.

In addition to the use of the above mentioned materials, the use of certain polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Other references disclosing polymeric polycarboxylic acids in oral compositions are South African Patent 720898, Sept. 12, 1972 which discloses such polymers having a molecular weight of from 1000 to 2,000,000; and U.S. Pat. No. 4,304,766, Dec. 8, 1971 to Chang discloses polyacrylic acid having a molecular weight in the range of 2,000 to 4,000,000 for use as a membrane to prevent the elution from teeth of previously applied agents. Finally U.S. Pat. No. 3,956,480, May 11, 1976 to Dichter discloses complexes of anionic polymers (e.g., acrylic acid) and a cationic therapeutic agent (e.g., chlorhexidine) as anticalculus agents.

In spite of the many disclosures in the anticalculus area, the need for improved products and methods still exist. The present invention is directed to the recognition that stannous ions when complexed with certain carboxylic acids or polyhydric alcohols provide anticalculus efficacy.

It is an object of the present invention therefore to provide methods for reducing calculus.

It is a further object of the present invention to provide methods utilizing stannous ions.

These and other objects will become clearer from the detailed description which follows.

All percentages and ratios used herein are by weight of the total composition unless otherwise specified. Additionally, all measurements are made at 25° C. in the composition or in an aqueous solution/dispersion unless otherwise specified.

SUMMARY OF THE INVENTION

The present invention embraces methods of reducing calculus utilizing an oral composition comprising:
(a) at least about 1000 ppm stannous ions;
(b) a mono or di carboxylic acid or polyhydric alcohol complexing agent having an equilibrium binding constant for stannous of less than about $10^5$; and
(c) a pharmaceutically acceptable carrier wherein said composition has a pH of from about 3.5 to about 7.0.

The compositions provide initial stannous levels required as well as maintaining those levels over extended time periods (e.g., one year at 25° C.). Additionally, the compositions provide stannous ions in a bioavailable form which can be taken up by plaque and inhibit crystal growth of calcium phosphate.

DETAILED DESCRIPTION OF THE INVENTION

The compositions useful in the methods of the present invention comprise stannous ions complexed with certain carboxylic acids or polyhydric alcohols and a pharmaceutically acceptable carrier.

By "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "ppm" as used herein is meant parts per million in the total composition.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

Stannous Ions

Stannous ions are the first essential component of the compositions used in the present methods. Suitable sources of stannous ions include stannous chloride, stannous acetate stannous bromide, and stannous glyconate among many others. The level of stannous ions, ppm, in a soluble state should be at least 1000, preferably from about 1500 to about 2500, most preferably from about 1750 to about 2250. These levels are of a toothpaste diluted one part paste with three parts water. In a mouthwash the levels are in the undiluted product. Other nonliquid product forms would be diluted in the same manner as toothpastes.

The stannous ions may be introduced into the compositions as a complex with the complexing agent or added in the form of a salt with materials other than the complexing agent.

Carboxylic Acid or Polyhydric Alcohols Complexing Agents

Suitable mono and di carboxylic acids useful in the present invention include acetic, lactic, gluconic, glycine, benzoic, tartaric, maleic and salicylic among many others. The acids may be used as free acids or in their water soluble salt forms (e.g., alkali metal salts). The polyhydric alcohols include such things as sorbitol, glycerine and polyethylene glycol.

The level of polycarboxylic acid is from about 0.01% to about 10%, preferably from about 0.5% to about 5% while the level of polyhydric alcohol is from about 10% to about 95%.

Pharmaceutically Acceptable Carrier

The carrier for the stannous ions and complexing components can be any vehicle suitable for use in the oral cavity. Such carriers include the usual components of mouthwashes, tooth-pastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrade dentin and do not provide calcium ions which may precipitate with, for example, the fluoride ions provided from stannous fluoride. These include, for example, silicas including gels and precipitates, insoluble sodium polymetaphosphate, $\beta$-phase calcium pyrophosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used. Abrasives such as calcium carbonate, calcium phosphate and regular calcium pyrophosphate are not preferred for use in the present compositions since they provide calcium ions which can complex $F^-$.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace and Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, July 29, 1982, incorporated herein by reference.

The abrasive in the compositions described herein is present at a level of from about 6% to about 70%, preferably from about 15% to about 25% when the dentifrice is a toothpaste. Higher levels, as high as 95%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

It is common to have water-soluble fluoride compound present in dentifrices and other oral compositions in an amount sufficient to give a fluoride ion concentration in the composition at 25° C. and/or when it is used of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al., U.S. Pat. No. 2,946,735, issued July 26, 1960 and Widder et al., U.S. Pat. No. 3,678,154, issued July 18, 1972 disclose such salts as well as others.

Water is also present in the toothpastes used in this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a total level of from about 15% to about 70%. This would include the amount of such materials included as complexing agents.

Also desirable for inclusion in the toothpastes of the present invention are antimicrobials such as quaternary ammonium salts, bis-biquanide salts, nonionic antimicrobial salts and flavor oils. Such agents are disclosed in U.S. Pat. No. 2,946,735, July 26, 1960, to Norris et al. and U.S. Pat. No. 4,051,234, Sept. 27, 1977 to Gieske et al., incorporated herein by reference. These agents, if present, are included at levels of from about 0.01% to about 1.5%.

Another preferred embodiment of the present invention is a mouthwash composition. Conventional mouthwash composition components can comprise the carrier for the anticalculus agent of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 18% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference.

The pH of the compositions used in the present method and/or its pH in the mouth can be any pH which is safe for the mouth's hard and soft tissues and will provide optimal effect of the stannous ions. Such pH's are from about 3.5 to about 7.0, preferably from about 4.0 to about 6.0, most preferably about 4.5.

METHOD OF MANUFACTURE

The carrier compositions used in the methods of the present invention can be made using methods which are common in the oral products area.

A specific method of manufacture is set forth in the Examples.

COMPOSITION USE

The present invention involves applying to the oral cavity safe and effective amounts of the compositions described herein. These amounts (e.g. from about 0.3 to about 15 g), if it is a toothpaste or mouthwash, are kept in the mouth for from about 15 to about 60 seconds.

The following examples further describe and demonstrate preferred embodiments within the scope of the present invention. The examples are given solely for illustration and are not to be construed as limitations of this invention as many variations thereof are possible without department from the spirit and scope thereof.

EXAMPLE IV

The following is a toothpowder of the present invention.

| Component | Wt. % |
|---|---|
| Stannous Fluoride | 0.454 |
| Stannous Chloride Dihydrate | 1.500 |
| Sodium Gluconate | 2.082 |
| Silica | 73.764 |
| Calcium Carbonate | 20.000 |
| Sodium Lauryl Sulfate | 1.000 |
| Flavor | 1.000 |
| Sodium Saccharin | 0.200 |

EXAMPLES V–VII

The following are topical gels of the present invention.

| Component | Weight % V | VI | VII |
|---|---|---|---|
| Stannous Fluoride | 0.454 | 0.454 | 0.454 |
| Stannous Chloride Dihydrate | 1.141 | 1.500 | 2.200 |
| Sodium Gluconate | 1.750 | 2.082 | 2.500 |
| Glycerin | 92.855 | 70.000 | 50.000 |
| Sorbitol (70% Soln.) | — | 21.964 | 42.146 |
| Sodium Carboxymethyl Cellulose | 0.600 | 0.800 | — |
| Hydroxyethyl Cellulose | — | — | 0.500 |
| Flavor | 1.000 | 1.000 | 1.000 |
| Sodium Saccharin | 0.200 | 0.200 | 0.200 |
| Sodium Alkyl Sulfate (27.9%) | 2.000 | 2.000 | 1.000 |

EXAMPLES VIII–X

The following are toothpastes representative of the present invention.

| Component | Weight % VIII | IX | X |
|---|---|---|---|
| Water | 12.500 | 12.500 | 13.500 |
| Sorbitol (70% Soln.) | 41.328 | 45.712 | 42.255 |
| Glycerin | 10.000 | 10.000 | 10.000 |
| PEG-12 | — | — | 3.000 |
| Titanium Dioxide | 0.525 | 0.525 | 0.525 |
| Silica | 20.000 | 20.000 | 20.000 |
| Na Carboxymethyl Cellulose | 1.000 | 1.000 | — |
| Na Carrageenan | 0.350 | 0.350 | 0.450 |
| Hydroxyethyl Cellulose | — | — | 0.400 |
| Na Alkyl Sulfate (27.9% Soln.) | 4.000 | 4.000 | 4.000 |
| Na Gluconate | 5.514 | 2.082 | 2.395 |
| Stannous Fluoride | 0.454 | 0.450 | 0.454 |
| Stannous Chloride Dihydrate | 2.198 | 1.500 | 1.140 |
| Na Saccharin | 0.230 | 0.230 | 0.230 |
| Flavor | 1.000 | 1.000 | 1.000 |
| FD&C Blue #1 (1% Soln.) | 0.051 | 0.051 | 0.051 |
| Na Hydroxide (50% Soln.) | 0.850 | 0.600 | 0.600 |
| pH | 4.5 | 4.5 | 4.5 |

In the above compositions, stannous chloride can be replaced by any of stannous bromide, stannous acetate, and stannous sulfate and sodium gluconate can be replaced by any of the following acids or their water soluble salts: acetic, lactic, glycine, benzoic, tartaric, maleic and salicylic with similar results obtained.

What is claimed is:

1. A method effective in reducing calculus comprising applying to dental enamel of subjects susceptible of forming calculus a safe and effective amount of a toothpaste composition containing:
   (a) at least 1000 ppm stannous ions from stannous chloride;
   (b) a mono or di carboxylic acid or polyhydric alcohol complexing agent having an equilibrium binding constant for stannous of less than about $10^5$ which is gluconic acid or a water soluble salt thereof;

(c) an acceptable toothpaste carrier; wherein the pH of said composition is from about 3.5 to about 7.0.

2. A method according to claim 1 wherein the stannous ion concentration is from about 1000 to about 2500 ppm.

3. A method according to claim 2 wherein the toothpaste also contains a silica dental abrasive.

4. A method according to claim 3 wherein the toothpaste also contains a fluoride ion source.

5. A method according to claim 4 wherein the fluoride ion source is stannous fluoride.

* * * * *